(12) United States Patent
Presti et al.

(10) Patent No.: US 12,427,095 B2
(45) Date of Patent: Sep. 30, 2025

(54) SPRAYABLE COMPOSITIONS

(71) Applicant: BEIERSDORF AG, Hamburg (DE)

(72) Inventors: Richard A. Presti, Kinnelon, NJ (US); Maria Cristina Niciporciukas, Easton, MD (US)

(73) Assignee: BEIERSDORF AG, Hamburg (DE)

( * ) Notice: Subject to any disclaimer, the term of this patent is extended or adjusted under 35 U.S.C. 154(b) by 968 days.

(21) Appl. No.: 17/422,529

(22) PCT Filed: Jan. 13, 2020

(86) PCT No.: PCT/US2020/013323
§ 371 (c)(1),
(2) Date: Jul. 13, 2021

(87) PCT Pub. No.: WO2020/150138
PCT Pub. Date: Jul. 23, 2020

(65) Prior Publication Data
US 2022/0096339 A1 Mar. 31, 2022

Related U.S. Application Data

(60) Provisional application No. 62/792,041, filed on Jan. 14, 2019.

(51) Int. Cl.
| | | |
|---|---|---|
| *A61Q 17/04* | (2006.01) | |
| *A61K 8/04* | (2006.01) | |
| *A61K 8/34* | (2006.01) | |
| *A61K 8/35* | (2006.01) | |
| *A61K 8/368* | (2006.01) | |
| *A61K 8/81* | (2006.01) | |
| *A61K 8/891* | (2006.01) | |

(52) U.S. Cl.
CPC .............. *A61K 8/046* (2013.01); *A61K 8/347* (2013.01); *A61K 8/35* (2013.01); *A61K 8/368* (2013.01); *A61K 8/8152* (2013.01); *A61K 8/891* (2013.01); *A61Q 17/04* (2013.01); *A61K 2800/591* (2013.01); *A61K 2800/80* (2013.01)

(58) Field of Classification Search
None
See application file for complete search history.

(56) References Cited

U.S. PATENT DOCUMENTS

| | | | |
|---|---|---|---|
| 2,879,231 A * | 3/1959 | Allen | A61K 8/046 510/120 |
| 2014/0030198 A1 | 1/2014 | Fares et al. | |
| 2014/0212363 A1 | 7/2014 | Harman et al. | |
| 2016/0374916 A1 * | 12/2016 | Halpern Chirch | A61Q 17/04 424/60 |
| 2017/0281488 A1 | 10/2017 | Halpern Chirch et al. | |
| 2018/0200176 A1 | 7/2018 | Li et al. | |
| 2019/0142709 A1 * | 5/2019 | Baldwin | A61K 8/347 222/394 |
| 2023/0295374 A1 * | 9/2023 | Bhattacharjee | C07C 69/14 524/109 |

FOREIGN PATENT DOCUMENTS

| | | | | |
|---|---|---|---|---|
| WO | WO-2015089035 A1 * | 6/2015 | | A61K 8/062 |
| WO | 2017197196 A1 | 11/2017 | | |
| WO | WO-2018209163 A1 * | 11/2018 | | A61K 8/042 |

OTHER PUBLICATIONS

Database GNPD [Online] Mintel; Jun. 26, 2018 (Jun. 26, 2018). anonymous: "Transparent Sun Protection Spray SPF 20" retrieved from www.gnpd.com Database accession No. 5779545.
Database GNPD [Online] Mintel; Aug. 1, 2017 (Aug. 1, 2017) anonymous: "Sublime Solar Oil SPF 30" retrieved from www.gnpd.com Database accession No. 4995943.
"Suncare compositions using amino hydroxy benzophenone derivatives". IP.com Journal. IP.com Inc. West Henrietta NY US Oct. 3, 2007 (Oct. 3, 2007) ISSN: 1533-0001.
"Sylvasol Polymers—Ethanol Sunscreen Sprays" IP.com Journal. IP.com Inc. West Henrietta NY US. Feb. 21, 2012 (Feb. 21, 2012) ISSN: 1533-0001.
"Sylvaclear Polymers in Sun Care". IP.com Journal. IP.com Inc. West Henrietta NY US Feb. 21, 2012 (Feb. 21, 2012) ISSN: 1533-0001.

* cited by examiner

*Primary Examiner* — Susan T Tran
(74) *Attorney, Agent, or Firm* — Abel Schillinger, LLP

(57) ABSTRACT

The present invention relates to sprayable compositions suitable for use in topical applications, for example, as sunscreen sprays. The sprayable compositions are alcohol-based. They include active agents, as well as a particular combination of film formers. The present invention also provides a method of using the sprayable compositions, and articles of manufacture containing the sprayable compositions.

18 Claims, No Drawings

SPRAYABLE COMPOSITIONS

TECHNICAL FIELD

The present disclosure relates generally to sprayable compositions. More specifically, the present disclosure relates to alcohol-based sprayable compositions, such as for topical applications, for example, sunscreen sprays.

DISCUSSION OF BACKGROUND INFORMATION

Consumers leading an active life and skin-smart consumers spending time outdoors look for a sunscreen product that applies easily, absorbs quickly, and leaves no undesirable white or sticky residue behind that would interfere with their activities. The sunscreen product also needs to be safe, for example, with respect to minimizing skin irritations.

Sprayable sunscreens can deliver on many of these desired attributes. Sprayable sunscreens based on alcohol solutions are a growing global product trend. They are generally easy to use and apply. They take little time to apply, dry quickly and typically do not exhibit the greasiness associated with traditional sunscreen lotions and creams.

Sprayable sport sunscreen products, which are intended to be sprayed directly onto wet skin, offer an advantage of more even coverage compared to traditional lotions and creams, and provide a more aesthetically pleasing look and feel. Further, when applied and working correctly, perform without a loss of efficacy in terms of broad spectrum sun protection and water resistance.

What is desired in the art are additional formulations suitable for use as sunscreen and other consumer products that delivers on the desired attributes noted above.

SUMMARY OF THE INVENTION

Provided herein are alcohol-based sprayable compositions. These compositions may be dispensed in the form of a spray, mist or fog. In some variations, the compositions provided reduce or eliminate skin irritations when applied. In certain variations, the compositions applied to a human do not induce sensitization; elicit a photoallergic response; and/or elicit a phototoxic response.

In some aspects, provided is a sprayable composition, comprising: at least one active agent; a combination of film formers, wherein the combination comprises (i) one or more oil-soluble film formers and (ii) one or more alcohol-soluble film formers and/or one or more water-soluble film formers; and at least one alcohol.

In some variations, the composition comprises two film formers, one of which is oil-soluble and the other of which is alcohol-soluble. For example, in certain variations, provided is a sprayable composition, comprising: at least one active agent; at least one oil-soluble film former; at least one alcohol-soluble carboxylated acrylic copolymer; and at least one alcohol. In one variation, provided is a sprayable composition, comprising: at least one active agent; two film formers selected from octyldodecyl/glyceryl hydroxy stearate dilinoleate dimethicone copolymer and a hydrophobic, high molecular weight carboxylated acrylic copolymer; and at least one alcohol.

In other variations, the composition comprises at least two film formers, one of which is oil-soluble and the other one of which is water-soluble. For example, in certain variations, provided is a sprayable composition, comprising: at least one active agent; one or more oil-soluble film formers; one or more water-soluble acrylates/C12-22 alkylmethacrylate copolymers; and at least one alcohol. In one variation, provided is a sprayable composition, comprising: at least one active agent; at least two film formers selected from octyldodecyl/glyceryl hydroxy stearate dilinoleate dimethicone copolymer and acrylates/C12-22 alkylmethacrylate copolymer; and at least one alcohol.

In some embodiments of the foregoing, the composition is a sprayable sunscreen composition, and the at least one active agent comprises one or more sunscreen active agents.

In one aspect, provided is an article of manufacture, such as a container comprising any of the compositions described herein, and a label containing instructions for use of the composition.

In yet other aspects, provided is a method of using any of the compositions described herein, comprising applying the compositions on a human, such as on the skin, scalp, lips and/or hair of a human.

DETAILED DESCRIPTION OF EMBODIMENTS OF THE INVENTION

The following description sets forth exemplary methods, parameters and the like. It should be recognized, however, that such description is not intended as a limitation on the scope of the present disclosure but is instead provided as a description of exemplary embodiments.

Provided herein are sprayable compositions. The compositions are alcohol-based. They include at least one active agent. They also include a combination of film formers. In some embodiments, the compositions comprise at least two film formers, including (i) at least one oil-soluble film former, and (ii) at least one alcohol-soluble film former and/or at least one water-soluble film former. In some variations, the compositions may also include other optional ingredients.

The various components of the sprayable compositions and methods of making and using such compositions are described in further detail below.

Active Agents

The sprayable compositions provided herein comprise at least one active agent. The active agents are typically skincare active agents. In some variations, skincare active agents may include materials regarded as acceptable for use as active skin-protecting ingredients. A skincare active agent may include, for example, skin protectant and/or anti-aging agent. Approval by a regulatory agency may sometimes be required for inclusion of active agents in formulations intended for human contact, including for example, sunscreen active ingredients or skin protectant ingredients such as petrolatum, white petrolatum, mineral oil, and dimethicone, as well as agents used as self-tanners.

The active agents present in the composition may differ based on the purpose of the sprayable composition. For example, a sprayable sunscreen composition comprises one or more sunscreen active agents.

Any suitable sunscreen active agents may be part of the sprayable sunscreen composition. Approved sunscreen active agents in the United States and elsewhere include, for example, paraaminobenzoic acid, avobenzone, cinoxate, dioxybenzone, homosalate, menthyl anthranilate, octocrylene, octyl methoxycinnamate, octyl salicylate, oxybenzone, 2-ethylhexyl 4-(dimethylamino)benzoate (e.g., Padimate O), phenylbenzimidazole sulfonic acid, octisalate, sulisobenzone, trolamine salicylate, titanium dioxide and zinc oxide. Several other sunscreen active ingredients are accepted for use in other countries. Examples from outside the U.S. include Tinosorb M, Tinosorb S, Uvinul T-150, UVA sorb HEB, Uvinul A Plus, Neo Heliopan AP, and Neo Heliopan MBC.

In some variations of the sprayable sunscreen compositions provided herein, the sunscreen active agents may be organic active agents or mineral active agents, or a combination thereof. In certain variations, the sprayable sunscreen composition comprises only organic active agents. Suitable organic active agents may include, for example, avobenzone, octocrylene, octisalate, and homosalate, as well as others listed above. In other variations, the sprayable sunscreen composition comprises only mineral active agents. Suitable mineral active agents may include, for example, titanium dioxide and zinc oxide. In yet other variations, the sprayable sunscreen composition comprises a combination of organic and mineral active agents, including any combinations of those described herein.

In certain embodiments, in addition to the skin-active ingredients already described, the sprayable compositions provided comprise one or more additional skin-active ingredients, such as a humectant and moisturizing ingredients, an anti-aging agent, a depigmenting agent, an anti-wrinkle agent, or an agent that treats oily skin. Additional active agents may include, for example, adenosine, hyaluronic acid, lanolin, citric acid, malic acid, lactic acid, tartaric acid, salicylic acid, a vitamin, a retinoid, retinol, retinoic acid, a carotenoid, an amino acid, a protein, an enzyme, and a coenzyme.

It is typical to use combinations of two or more skincare active agents in a formulation. The amount of skincare active agent or agents may be present in an amount that is consistent with the guidelines of the FDA or other regulatory bodies. The use of a combination of active agents is especially true for sunscreen formulations to achieve higher levels of ultraviolet absorption or to provide useful absorption over a wider range of ultraviolet wavelengths than can be the case with a single active component. Preferably, the sunscreen active agent or agents is present in an amount that is consistent with the FDA sunscreen monograph for sunscreen active agent or agents that are believed to provide the requisite SPF in accordance with the FDA monograph for such sunscreens. Other skin care active agents may include, for example, sunless tanning active agents, skin protectant active agent emollients, and insect repelling agents.

In some variations, the one or more active agents are present in the compositions herein between 10% and 40%, between 20% and 40%, or between 20% and 35% by weight of the composition.

Film Formers

The sprayable compositions provided herein comprise a combination of film formers. In some embodiments, the combination comprises (i) one or more oil-soluble film formers and (ii) one or more alcohol-soluble film formers and/or one or more water-soluble film formers. For example, in one embodiment, the combination comprises one or more oil-soluble film formers and one or more alcohol-soluble film formers. In another embodiment, the combination comprises one or more oil-soluble film formers and one or more water-soluble film formers. In yet another embodiment, the combination comprises one or more oil-soluble film formers, one or more alcohol-soluble film formers, and one or more water-soluble film formers.

In some variations, the one or more oil-soluble film formers comprise a polyester. In certain variations, the oil-soluble film former is or comprises a glycerin polyester. In another variation, the polyester has terminal silicone modifications. Other such polyesters are described in U.S. Pat. No. 8,808,676.

In other variations, the one or more oil-soluble film formers comprise a polyamide.

In yet other variations, the one or more oil-soluble film formers comprise a copolymer of at least one olefin and at least one unsaturated fatty acid.

Suitable oil-soluble film formers may include, for example, octyldodecyl/glyceryl hydroxy stearate dilinoleate dimethicone copolymer (e.g., Polyester-27), polyamide-8 (e.g., Oleocraft™ LP-20, Croda), polyamide-3 (e.g., Oleocraft™ HP-31, Croda), C28-52 olefin/undecylenic acid copolymer (e.g., Performa™ V 6112, New Phase Technologies).

In some variations, the one or more alcohol-soluble film formers comprise an acrylic copolymer. In certain variations, the one or more alcohol-soluble film formers comprise a carboxylated acrylic copolymer. In certain variations, the one or more alcohol-soluble film formers comprise a hydrophobic, carboxylated acrylic copolymer.

Suitable alcohol-soluble film formers may include, for example, a hydrophobic, high molecular weight carboxylated acrylic copolymer (e.g., Dermacryl® 79, AkzoNobel Surface Chemistry).

In some variations, the one or more water-soluble film formers comprise a copolymer of acrylates.

Suitable water-soluble film formers may include, for example, acrylates/C12-22 alkylmethacrylate copolymer, which may be the tetrapolymer emulsion polymerization product of methacrylic acid, methyl methacrylate, butyl acrylate and cetyl-eicosinyl methacrylate (e.g., Allianz™ OPT and Allianz™ OPT C5G, Ashland).

For example, in some variations, the combination comprises octyldodecyl/glyceryl hydroxy stearate dilinoleate dimethicone copolymer and an acrylic copolymer. In certain variations, the acrylic copolymer is a carboxylated acrylic copolymer. In certain variations, the acrylic copolymer is a high molecular weight carboxylated acrylic copolymer. In one variation, the acrylic copolymer is a hydrophobic, carboxylated acrylic copolymer. In another variation, the acrylic copolymer is a hydrophobic, high molecular weight carboxylated acrylic copolymer. In certain variations, the combination comprises octyldodecyl/glyceryl hydroxy stearate dilinoleate dimethicone copolymer and acrylates/alkylmethacrylate copolymer. In other variations, the combination comprises octyldodecyl/glyceryl hydroxy stearate dilinoleate dimethicone copolymer and acrylates/C12-22 alkylmethacrylate copolymer.

In some embodiments, (at least) two film formers are present. For example, in certain variations, the combination consists of, or consists essentially of, octyldodecyl/glyceryl hydroxy stearate dilinoleate dimethicone copolymer and an acrylic copolymer (including any of the variations described herein). In one variation, the combination consists of, or consists essentially of, octyldodecyl/glyceryl hydroxy stearate dilinoleate dimethicone copolymer and a hydrophobic, carboxylated acrylic copolymer. In another variation, the combination consists of, or consists essentially of, octyldodecyl/glyceryl hydroxy stearate dilinoleate dimethicone copolymer and a hydrophobic, high molecular weight carboxylated acrylic copolymer. In certain variations, the combination consists of, or consists essentially of, octyldodecyl/glyceryl hydroxy stearate dilinoleate dimethicone copolymer and acrylates/alkylmethacrylate copolymer. In another variation, the combination consists of, or consists essentially of, octyldodecyl/glyceryl hydroxy stearate dilinoleate dimethicone copolymer and acrylates/C12-22 alkylmethacrylate copolymer.

Alcohol

In certain embodiments, the sprayable composition further comprises about 40% to about 90%, about 50% to 90%, about 50% to about 80%, about 60% to about 80%, about 65% to about 75%, or about 65% to 70% of at least one alcohol (by weight of the composition). In certain variations when the sprayable composition is a sunscreen composition having a SPF rating, the amount of alcohol present in the composition may range from as low as 50% (for example, in compositions having a SPF rating of 100) to greater than 80% (for example, in compositions having a SPF rating of 15).

Any suitable alcohol may be used. In certain embodiments, an alcohol that is suitable for skincare is used. In certain embodiments, the alcohol comprises a short-chain alcohol (e.g., an alcohol having from 1 to 4 carbon atoms). In certain embodiments, the alcohol is ethanol, methanol, or isopropanol, or blends thereof. In certain embodiments, the alcohol is denatured. In some embodiments, the alcohol is denatured ethanol (e.g., SD alcohol 40-B).

Other Ingredients

The sprayable compositions provided herein may contain a wide range of additional, optional components. For example, a wide variety of cosmetic and pharmaceutical ingredients commonly used in skincare formulations may be suitable for use in the sprayable compositions herein. Examples of these functional classes disclosed in these references include, for example, absorbents, abrasives, anticaking agents, antioxidants, binders, biological additives, buffering agents, bulking agents, chelating agents, chemical additives, colorants, cosmetic astringents, cosmetic biocides, cryoprotectants, stabilizers, denaturants, drug astringents, external analgesics, film formers, fragrance components, humectants, pacifying agents, pH adjusters, plasticizers, preservatives, propellants, reducing agents, skin bleaching agents, skin-conditioning agents (emollients, humectants, miscellaneous, and occlusive), skin protectants, solvents, SPF enhancers/boosters, hydrotropes, sunscreen agents, ultraviolet light absorbers, and viscosity increasing agents.

In certain embodiments, the sprayable composition further comprises one or more stabilizers. In one embodiment, the sprayable composition further comprises a singlet quencher or a triplet quencher, or a combination thereof. In some variations, the sprayable composition further comprises ethylhexyl methoxycrylene (e.g., SolaStay® S1, Hallstar). Other suitable stabilizers may include, for example, diethylhexyl 2,6-naphthalate (e.g., Corapan® TQ, Symrise), Polyester-8 (e.g., Polycrylene®, Hallstar), and undecylcrylene dimethicone (e.g., Hallbrite® PSF, Hallstar).

In certain embodiments, the sprayable composition further comprises one or more solubilizers. In some variations, the sprayable composition further comprises neopentyl glycol diheptanoate (e.g., LexFeel®, Inolex).

In certain embodiments, the sprayable composition further comprises one or more emollients. An emollient generally helps to smooth and soften the skin, and may also reduce its roughness, cracking or irritation. In some variations, the sprayable composition further comprises a silicone fluid (e.g., Xiameter®, Dow Corning). Other suitable emollients may include, for example, mineral oil (e.g., mineral oil having a viscosity in the range of 50 to 500 centipoise), lanolin oil, coconut oil, cocoa butter, olive oil, almond oil, macadamia nut oil, aloe extracts such as aloe vera lipoquinone, synthetic jojoba oils, natural Sonora jojoba oils, safflower oil, corn oil, liquid lanolin, cottonseed oil and peanut oil. In certain variations, the emollient may include a cocoglyceride, which is a mixture of mono, di and triglycerides of cocoa oil, or dicaprylyl ether. In other variations, the emollient may include squalane, castor oil, polybutene, sweet almond oil, avocado oil, calophyllum oil, ricin oil, vitamin D, vitamin E acetate, olive oil, silicone fluids (e.g., polydimethylsiloxane and cyclomethicone), linotenic alcohol, oleyl alcohol, the oil of cereal germs such as the oil of wheat germ, isopropyl palmitate, cotyle palmitate, isopropyl myristate, hexadecyl stearate, butyl stearate, decyl oleate, acetyl glycerides, octanoates and benzoates of (C12-C15) alcohols, the octanoates and decanoates of alcohols and poly-alcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe Vera extract. In yet other variations, other suitable emollients that are solids or semi solids at ambient temperatures may be used. Such solid or semi-solid cosmetic emollients include, for example, glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate.

In certain embodiments, the sprayable composition further comprises humectants and/or moisturizing ingredients.

In other embodiments, the sprayable composition further comprises depigmenting agents. Suitable depigmenting agents may include, for example, vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts.

In other embodiments, the sprayable composition further comprises anti-wrinkle actives. In some variations, an anti-wrinkle active may include a natural or synthetic compound producing a biological effect, such as the increased synthesis and/or activity of certain enzymes, when brought into contact with an area of wrinkled skin, this has the effect of reducing the appearance of wrinkles and/or fine lines.

In other embodiments, the sprayable composition further comprises a skin-active ingredient that addresses oily skin. These actives can be sebo-regulating or antiseborrhoeic agents capable of regulating the activity of sebaceous glands. These include, for example and without limitation: retinoic acid, benzoyl peroxide, sulfur, and vitamin B6.

In certain embodiments, the sprayable composition further comprises one or more antioxidants. An antioxidant is a natural or synthetic substance, which may be added to the compositions described herein (including, for example, sunscreen compositions) to protect from or delay its deterioration due to the action of oxygen in the air (oxidation) and to protect the skin from sun damage. Antioxidants prevent oxidative deterioration which may lead to the generation of rancidity and nonenzymatic browning reaction products. Suitable antioxidants may include, for example, propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Oxynex (Oxynex® ST Liquid, Merck KGaA, which is a mixture of diethylhexyl syringylidenemalonate and caprylic/capric triglyceride), Vitamin A, Vitamin E and Vitamin C. One or more antioxidants can optionally be included in the compositions herein, for example, in an amount ranging from about 0.001% to about 5%, or about 0.01% to about 0.5% (by weight of the composition).

In certain embodiments, the sprayable composition further comprises one or more vitamin(s). Suitable vitamins may include, for example, ascorbic acid, vitamin A, vitamin E, vitamin B, glycolic acid, and allantoin.

In yet other embodiments, the sprayable composition further comprises one or more fragrance(s). Fragrances are generally aromatic substances which can impart an aesthetically pleasing aroma to the skincare or sunscreen compositions, and may be part of the sprayable compositions provided herein. Suitable fragrances may include, for example, aromatic materials extracted from botanical sources (e.g., rose petals, gardenia blossoms, jasmine flowers) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. Both types are considered to be within the scope of the present invention.

It should generally be understood that some of the ingredients described herein may fall within one or more functional classes. For example, neopentyl glycol diheptanoate (e.g., LexFeel®, Inolex) may be an emollient as well as solubilizer when used in the sprayable compositions described herein.

Safety Characteristics of the Sprayable Compositions

In some embodiments, when the compositions described herein are applied to a human, such as on the skin, the compositions minimize or do not cause dermal irritation. Dermal irritation may occur when erythema and/or edema are observed. In some variations, when the compositions applied do not cause dermal irritation, no visible skin reaction is observed.

In some embodiments, when the compositions described herein are applied to a human, such as on the skin, the compositions minimize or do not induce sensitization. Sensitization may occur when erythema, edema and/or itching and/or presence of papules are observed. In some variations, when the compositions applied do not induce sensitization, no visible skin reaction is observed, or barely perceptible erythema or mild erythema is observed.

In other embodiments, when the compositions described herein are applied to a human, such as on the skin, the compositions minimize or do not elicit a photoallergic response. A photoallergic response is generally understood to be an allergic reaction that causes inflammation of the skin in the sun-exposed areas.

In other embodiments, when the compositions described herein are applied to a human, such as on the skin, the compositions minimize or do not elicit a phototoxic response. A phototoxic response may include burning and/or stinging sensation, as well as potential redness from exposure to the sun in the exposed areas of the body.

Methods of Making the Sprayable Compositions

In certain aspects, provided herein is a method of manufacturing the sprayable compositions described herein. In some embodiments, the method comprises:

Combining the one or more oil-soluble film formers with the one or more active agents to form a first mixture, wherein the first mixture comprises an oil phase;

mixing and heating the first mixture until the oil phase of the first mixture is at least partially or fully dissolved; and adding at least one alcohol and at least one water-soluble film former to the first mixture to produce the composition.

In one variation, the method comprises:

combining the one or more oil-soluble film formers with the one or more active agents to form a first mixture, wherein the first mixture comprises an oil phase;

mixing and applying heat to the first mixture until the oil phase of the first mixture is at least partially or fully dissolved;

removing heat applied; adding at least one alcohol and at least one water-soluble film former to the first mixture to produce a second mixture; and mixing the second mixture until all ingredients therein are at least partially or fully dissolved to produce the composition.

In certain embodiments of the foregoing, oil-soluble film former and active agent may be further combined with additional ingredients, such as emollients and fragrances. In certain embodiments of the foregoing, alcohol and water-soluble film former may be further combined with additional ingredients, such as emollients and fragrances.

Use of the Sprayable Compositions

In some aspects, provided is a method of applying the sprayable compositions described herein. In some embodiments, provided is a method comprising applying any of the compositions described herein onto skin, scalp, lips and/or hair of a human.

In other aspects, provided is a system to dispense the sprayable compositions described herein. In one aspect, provided is an article of manufacture, such as a container comprising any of the compositions described herein, and a label containing instructions for use of the composition. In some embodiments, the container is a bag-on-valve. In other variations, the container is an aerosol container, or a container with a pump spray or a trigger spray.

In some variations of the foregoing methods and systems, the sprayable composition may be applied onto wet skin of a human.

EXAMPLES

The following Examples are merely illustrative and are not meant to limit any aspects of the present disclosure in any way.

Example 1A

Exemplary Sunscreen Spray Formulation ("Formulation A")

This example describes an exemplary sunscreen spray formulation of the disclosure in Table 1 below, and methods of manufacturing thereof.

TABLE 1

| Formulation A | |
|---|---|
| Ingredient Description | Dry Percent w/w |
| Part A Ingredients | |
| Octyldodecyl/glyceryl hydroxy stearate dilinoleate dimethicone copolymer | 1.50 |

TABLE 1-continued

Formulation A

| Ingredient Description | Dry Percent w/w |
|---|---|
| Vitamin E | 0.25 |
| Octisalate | 5.00 |
| Avobenzone | 3.00 |
| Homosalate | 10.00 |
| Octocrylene | 5.00 |
| Neopentyl Glycol Diheptanoate | 5.00 |
| Vitamin C | 0.01 |
| Part B Ingredients | |
| Alcohol | 68.14 |
| Dermacryl ® 79 | 1.00 |
| Silicone fluid | 1.00 |
| Fragrance | 0.10 |
| Total | 100.00 |

The formulation in Table 1 above was prepared as follows: All the ingredients in Part A of Table 1 were added to a container, and heated to 135-145° F. with mixing. After the oil phase of Part A was observed to be dissolved, heat was removed. Then, all the ingredients of Part B in Table 1 were added to the container, and mixed until all ingredients were observed to be dissolved.

Example 1B

Comparison Sunscreen Spray Formulation ("Comparison Formulation")

This example describes a comparison sunscreen spray formulation in Table 2 below, and methods of manufacturing thereof.

TABLE 2

Comparison Formulation

| Ingredient Description | Dry Percent w/w |
|---|---|
| Part A Ingredients | |
| Octyldodecyl/glyceryl hydroxy stearate dilinoleate dimethicone copolymer | 1.50 |
| SolaStay S1 | 0.25 |
| Vitamin E | 0.25 |
| Avobenzone | 3.00 |
| Octocrylene | 7.50 |
| Octisalate | 4.50 |
| Homosalate | 9.00 |
| Neopentyl Glycol Diheptanoate | 3.00 |
| Vitamin C | 0.01 |
| Part B Ingredients | |
| Alcohol | 70.89 |
| Fragrance | 0.10 |
| Total | 100.00 |

The formulation in Table 2 above was prepared as follows: All the ingredients in Part A of Table 2 were added to a container, and heated to 125-135° F. with mixing. After the oil phase of Part A was observed to be dissolved, heat was removed. Then, all the ingredients of Part B in Table 2 were added to the container, and mixed until all ingredients were observed to be dissolved.

Example 2A

Clinical Study of Formulation A

This example describes a clinical study of Formulation A using a Repeated Insult Patch Test. The objective of this study was to determine the dermal irritation and sensitization potential of test material(s) in a representative population of subjects. Panel results of 5% or more subjects scoring 1+ or more during the induction phase are indicative of formula irritation. One or more erythema scores of 2+ or higher and/or edema and/or itching and/or presence of papules in the challenge phase is indicative of sensitization.

Test Material

The test material used in this study was Formulation A.

Study Evaluations

The following Dermal Scoring System was used.

| Dermal Score | Description |
|---|---|
| 0 | No visible skin reaction |
| ± | Barely perceptible erythema |
| 1+ | Mild erythema |
| 2+ | Well defined erythema |
| 3+ | Severe erythema and edema |
| 4+ | Erythema and edema with vesiculation |

In addition, number of sites presenting edema (e), itching (It) and papules (Pa) were annotated.

Test Method Summary

The test article was evaluated over a six-week period using an occlusive patch procedure involving 3 phases: (1) Induction, (2) Rest, and (3) Challenge. The induction phase included nine consecutive applications of the test article covered by an occlusive patch and subsequent evaluation of the patch sites at 48-hr intervals (72-hr on weekends). Following the 9th evaluation, the subjects were dismissed for the 10-21 day rest phase. During the challenge phase, subjects had product applied under identical patching conditions to the original induction site and to sites previously unexposed to the test article. Patches were removed 48-hrs later and the sites were evaluated. Identical product application and patching conditions were applied to the same sites and evaluated after 48-hrs for a total exposure of 96-hrs during the challenge phase.

Results

A total of 109 subjects completed the study. Table 3 below summarizes the number of subjects exhibiting each Dermal Score.

TABLE 3

Summary of Dermal Scores

| Reading scores | Induction Scores Applications | | | | | | | | | Challenge Scores Time after challenge patch | | |
|---|---|---|---|---|---|---|---|---|---|---|---|---|
| | 1 | 2 | 3 | 4 | 5 | 6 | 7 | 8 | 9 | 24 Hour | 48 Hour | 72 Hour |
| 0 | 110 | 105 | 108 | 106 | 109 | 109 | 107 | 107 | 109 | 108 | 108 | 109 |
| +/− | 1 | 4 | 1 | 3 | 0 | 0 | 2 | 2 | 0 | 1 | 1 | 0 |
| +1 | 0 | 0 | 0 | 0 | 0 | 0 | 0 | 0 | 0 | 0 | 0 | 0 |
| +2 | 0 | 0 | 0 | 0 | 0 | 0 | 0 | 0 | 0 | 0 | 0 | 0 |

TABLE 3-continued

Summary of Dermal Scores

| Reading scores | Induction Scores Applications | | | | | | | | | Challenge Scores Time after challenge patch | | |
|---|---|---|---|---|---|---|---|---|---|---|---|---|
| | 1 | 2 | 3 | 4 | 5 | 6 | 7 | 8 | 9 | 24 Hour | 48 Hour | 72 Hour |
| +3 | 0 | 0 | 0 | 0 | 0 | 0 | 0 | 0 | 0 | 0 | 0 | 0 |
| +4 | 0 | 0 | 0 | 0 | 0 | 0 | 0 | 0 | 0 | 0 | 0 | 0 |
| Total | 111 | 109 | 109 | 109 | 109 | 109 | 109 | 109 | 109 | 109 | 109 | 109 |

Conclusion

Under the conditions of this study, Formulation A did not demonstrate a potential for eliciting dermal irritation or inducing sensitization.

Example 2B

Clinical Study of Comparison Formulation

This example describes a clinical study of Comparison Formulation using a Repeated Insult Patch Test. The objective of this study was to determine the dermal irritation and sensitization potential of test material(s) in a representative population of subjects. Panel results of 5% or more subjects scoring 1+ or more during the induction phase are indicative of formula irritation. One or more erythema scores of 2+ or higher and/or edema and/or itching and/or presence of papules in the challenge phase is indicative of sensitization.

Test Material

The test material used in this study was Comparison Formulation.

Study Protocol

The clinical protocol for this example follows the protocol set forth in Example 2A above.

Results

A total of 109 subjects completed the study. Table 4 below summarizes the number of subjects exhibiting each Dermal Score.

Conclusion

Under the conditions of this study, Comparison Formulation may have a potential for eliciting dermal irritation as well as inducing sensitization.

Example 3A

Clinical Study of Formulation A

This example describes another clinical study of Formulation A, involving a photoallergy test. The objective of this study was to evaluate the potential of a test material to produce a photoallergic response. One or more erythema scores of 2+ or higher and/or edema and/or itching and/or presence of papules during challenge and not cleared by re-challenge phase is indicative of sensitization response. If erythema scores in the irradiated sites are higher than non-irradiated, the responses are considered photoallergic in nature.

Test Material

The test material used in this study was Formulation A.

Study Protocol

The procedure involved repeated, 24 hour patches of the test article on two sites on the lower or mid back, reapplication of the test article on one of the two sites before irradiation. The re-applied site was then irradiated with 3X Minimal Erythemal Dose (MED) UVA/UVB ultraviolet light irradiation for products containing sunscreens and 2X MED for products that did not contain sunscreens. Patch/irradiation occurred six times over a 3 week period followed by a 9-16 day rest (non-treatment) period. In the challenge phase, 24-hour patches of the test article were applied to two virgin sites. Additionally, a third site was patched without treatment. After removal of the patches, the test article was then reapplied to one site of the two sites with test article and the re-applied site was then irradiated with 0.5 MED of UVA/UVB and 10 J/cm$^2$ of UVA. The untreated site was also irradiated at this time with the same dose of irradiation. Reactions were graded 24, 48, and 72 hours after irradiation.

Results

A total of 52 subjects completed the study. Table 5 below summarizes the number of subjects exhibiting each Dermal Score. Table 6 below summarizes data from the re-challenge phase for one of the subjects.

TABLE 4

Summary of Dermal Scores

| Reading scores | Induction Scores Applications | | | | | | | | | Challenge Scores Time after challenge patch | | |
|---|---|---|---|---|---|---|---|---|---|---|---|---|
| | 1 | 2 | 3 | 4 | 5 | 6 | 7 | 8 | 9 | 24 Hour | 48 Hour | 72 Hour |
| 0 | 107 | 104 | 103 | 103 | 103 | 94 | 94 | 94 | 102 | 105 | 88 | 91 |
| +/− | 4 | 5***, ** | 7 | 7 | 7*** | 15* | 16 | 16***, ** | 8*** | 5 | 18 | 12**, @ |
| +1 | 1 | 3 | 2* | 2 | 1 | 1 | 1**** | 1 | 1 | 1 | 5* | 6***, @ |
| +2 | 0 | 0 | 0 | 0 | 0 | 1*** | 0 | 0 | 0 | 0 | 0 | 0 |
| +3 | 0 | 0 | 0 | 0 | 0 | 0 | 0 | 0 | 0 | 0 | 0 | 0 |
| +4 | 0 | 0 | 0 | 0 | 0 | 0 | 0 | 0 | 0 | 0 | 0 | 0 |
| Total | 112 | 112 | 112 | 112 | 111 | 111 | 111 | 111 | 111 | 111 | 111 | 109 |

*1 site presented itching
**1 site presented papulae
***2 sites presented itching
****4 sites presented itching
@ patched sites presented reactions at 96 hrs

TABLE 5

Summary of Dermal Scores
Number of Subjects Exhibiting Each Dermal Score

| | Induction Phase | | | | | | | | | | Challenge Phase | | | | | | | | | | | |
|---|---|---|---|---|---|---|---|---|---|---|---|---|---|---|---|---|---|---|---|---|---|---|
| | 1 | | 2 | | 3 | | 4 | | 5 | | Immediate | | | 24 Hour | | | 48 Hour | | | 72 Hour | | |
| Scores | I | NI | I | NI | I | NI | I | NI | I | NI | I | NI | C | I | NI | C | I | NI | C | I | NI | C |
| 0 | 53 | 53 | 53 | 53 | 52 | 52 | 51 | 52 | 52 | 51 | 47 | 50 | 52 | 49 | 51 | 52 | 50 | 51 | 52 | 50 | 52 | 52 |
| ± | 0 | 0 | 0 | 0 | 0 | 0 | 1 | 0 | 0 | 1 | 5 | 2 | 0 | 2 | 1 | 0 | 1 | 1 | 0 | 2* | 0 | 0 |
| 1 | 0 | 0 | 0 | 0 | 0 | 0 | 0 | 0 | 0 | 0 | 0 | 0 | 0 | 1* | 0 | 0 | 1* | 0 | 0 | 0 | 0 | 0 |
| 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Total | 53 | 53 | 53 | 53 | 52 | 52 | 52 | 52 | 52 | 52 | 52 | 52 | 52 | 52 | 52 | 52 | 52 | 52 | 52 | 52 | 52 | 52 |

*1 site presented edema
I = Irradiated Site (Treated)
NI = Non-Irradiated Site (Treated)
CI = Control Irradiated Site
CNI = Control Non-Irradiated Site

TABLE 6

Data from re-challenge phase

| | Re-Challenge Phase Post-Irradiation | | | | | | | | | | | |
|---|---|---|---|---|---|---|---|---|---|---|---|---|
| Number of | Immediate | | | 24 Hours | | | 48 Hours | | | 72 Hours | | |
| Subjects | I | NI | C | I | NI | C | I | NI | C | I | NI | C |
| 1 | ± | ± | 0 | ± | ± | 0 | ± | ± | 0 | 0 | 0 | 0 |

Conclusion

Under the conditions of this study, the test material did not induce a photoallergy response.

Example 3B

Clinical Study of Comparison Formulation

This example describes another clinical study of Comparison Formulation, involving a photoallergy test. The objective of this study was to evaluate the potential of a test material to produce a photoallergic response. One or more erythema scores of 2+ or higher and/or edema and/or itching and/or presence of papules during challenge and not cleared by re-challenge phase is indicative of sensitization response. If erythema scores in the irradiated sites are higher than non-irradiated, the responses are considered photoallergic in nature.

Test Material

The test material used in this study was Comparison Formulation.

Study Protocol

The clinical protocols for this example follows the protocols set forth in Example 3A above.

Results

A total of 50 subjects completed the study. Table 7 below summarizes the number of subjects exhibiting each Dermal Score. Table 8 below summarizes data from the re-challenge phase for one of the subjects.

TABLE 7

Summary of Dermal Scores

| | Induction Phase | | | | | | | | | | Challenge Phase | | | | | | | | | | | |
|---|---|---|---|---|---|---|---|---|---|---|---|---|---|---|---|---|---|---|---|---|---|---|
| | 1 | | 2 | | 3 | | 4 | | 5 | | Immediate | | | 24 Hour | | | 48 Hour | | | 72 Hour | | |
| Scores | I | NI | I | NI | I | NI | I | NI | I | NI | I | NI | C | I | NI | C | I | NI | C | I | NI | C |
| 0 | 41 | 41 | 45 | 42 | 51 | 48 | 49 | 48 | 47 | 45 | 37 | 36 | 51 | 36 | 39 | 51 | 40 | 41 | 51 | 43 | 44 | 50 |
| ± | 8 | 7 | 6 | 8 | 0 | 3 | 1 | 2 | 4 | 5** | 11 | 13 | 0 | 14* | 11 | 0 | 10** | 9 | 0 | 6 | 5 | 0 |
| 1 | 3 | 4 | 1 | 2 | 0 | 0 | 1 | 1 | 0 | 1 | 3*** | 2*** | 0 | 0 | 0 | 0 | 0 | 0 | 0 | 1** | 0 | 0 |
| 2 | 0 | 0 | 0 | 0 | 1* | 1* | 0 | 0 | 0 | 0 | 0 | 0 | 0 | 1**, *** | 1**, *** | 0 | 1**, *** | 1**, *** | 0 | 1**, *** | 0 | 0 |

TABLE 7-continued

Summary of Dermal Scores

| | Induction Phase | | | | | | | | | | Challenge Phase | | | | | | | | | | |
|---|---|---|---|---|---|---|---|---|---|---|---|---|---|---|---|---|---|---|---|---|---|
| | 1 | | 2 | | 3 | | 4 | | 5 | | Immediate | | | 24 Hour | | | 48 Hour | | | 72 Hour | | |
| Scores | I | NI | I | NI | I | NI | I | NI | I | NI | I | NI | C | I | NI | C | I | NI | C | I | NI | C |
| 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Total | 52 | 52 | 52 | 52 | 52 | 52 | 51 | 51 | 51 | 51 | 51 | 51 | 51 | 51 | 51 | 51 | 51 | 51 | 51 | 50 | 50 | 50 |

*1 site presented papule
**1 site presented itching
***1 site presented edema
I = Irradiated Site (Treated)
NI = Non-Irradiated Site (Treated)
CI = Control Irradiated Site
CNI = Control Non-Irradiated Site
*Itching in one subject

TABLE 8

Data from re-challenge phase

| | Re-challenge Phase Post-Irradiation | | | | | | | | | | | |
|---|---|---|---|---|---|---|---|---|---|---|---|---|
| Number of | Immediate | | | 24 Hours | | | 48 Hours | | | 72 Hours | | |
| subjects | I | NI | C | I | NI | C | I | NI | C | I | NI | C |
| 1 | ± | ± | 0 | 1 + It, e | 2 + It, e | 0 | 1 + It, e | 2 + It, e | 0 | 1 + It, e | 2 + It, e | 0 |

Conclusion

Under the conditions of this study, Comparison Formulation did not produce a photoallergic response. However, the presence of erythema, itching and edema in the re-challenge phase is indicative of sensitization in one subject.

Example 4A

Clinical Study of Formulation A

This example describes another clinical study of Formulation A, involving a phototoxicity test. The objective of this study was to determine the phototoxic potential of a topically applied article in human subjects. If erythema scores in the irradiated sites are higher than non-irradiated, the responses are considered phototoxic in nature. Pre-sensitization can be captured in this study if subjects present erythema scores of 2+ or higher and/or edema, and/or itching and/or papules even during a re-challenge.

Test Material

The test material used in this study was Formulation A.

Study Protocol

The procedure involved a one-time application of test article(s) to duplicate sites on the lower or mid-back for 24 hours. After removal of the patches, the material was reapplied to one site, and irradiated between 5 and 15 minutes after reapplication. The duplicate site served as an unirradiated control. Two more sites were patched with an untreated patch. One of them was irradiated after patch removal. Reactions were graded immediately, twenty-four (24) and forty-eight (48) hours after irradiation.

Results

A total of 35 subjects completed the study. Table 9 below summarizes the number of subjects exhibiting each Dermal Score.

TABLE 9

Summary of Dermal Scores
Number of Subjects Exhibiting Each Dermal Score

| | Pre-Irradiation 24 Hour Patch | | | | Post-Irradiation | | | | | | | | | | | |
|---|---|---|---|---|---|---|---|---|---|---|---|---|---|---|---|---|
| | Removal | | | | Immediate/10 min | | | | 24 Hours | | | | 48 Hours | | | |
| Scores | I | NI | CI | CNI | I | NI | CI | CNI | I | NI | CI | CNI | I | NI | CI | CNI |
| 0 | 32 | 33 | 35 | 35 | 30 | 32 | 31 | 35 | 33 | 34 | 34 | 35 | 34 | 34 | 35 | 35 |
| ± | 3 | 2 | 0 | 0 | 4 | 2 | 4 | 0 | 2 | 0 | 1 | 0 | 0 | 0 | 0 | 0 |
| 1+ | 0 | 0 | 0 | 0 | 1 | 1 | 0 | 0 | 0 | 1* | 0 | 0 | 1* | 1* | 0 | 0 |
| 2+ | 0 | 0 | 0 | 0 | 0 | 0 | 0 | 0 | 0 | 0 | 0 | 0 | 0 | 0 | 0 | 0 |

TABLE 9-continued

Summary of Dermal Scores
Number of Subjects Exhibiting Each Dermal Score

| | Pre-Irradiation 24 Hour Patch Removal | | | | Post-Irradiation | | | | | | | | | | | |
|---|---|---|---|---|---|---|---|---|---|---|---|---|---|---|---|---|
| | | | | | Immediate/10 min | | | | 24 Hours | | | | 48 Hours | | | |
| Scores | I | NI | CI | CNI | I | NI | CI | CNI | I | NI | CI | CNI | I | NI | CI | CNI |
| 3+ | 0 | 0 | 0 | 0 | 0 | 0 | 0 | 0 | 0 | 0 | 0 | 0 | 0 | 0 | 0 | 0 |
| 4+ | 0 | 0 | 0 | 0 | 0 | 0 | 0 | 0 | 0 | 0 | 0 | 0 | 0 | 0 | 0 | 0 |
| Total | 35 | 35 | 35 | 35 | 35 | 35 | 35 | 35 | 35 | 35 | 35 | 35 | 35 | 35 | 35 | 35 |

I = Irradiated Site (Treated)
NI = Non-Irradiated Site (Treated)
CI = Control Irradiated Site
CNI = Control Non-Irradiated Site Conclusion Under the conditions of this study, Formulation A did not elicit a phototoxic response.

Example 4B

Clinical Study of Comparison Formulation

This example describes another clinical study of Comparison Formulation, involving a phototoxicity test. The objective of this study was to determine the phototoxic potential of a topically applied article in human subjects. If erythema scores in the irradiated sites are higher than non-irradiated, the responses are considered phototoxic in nature. Pre-sensitization can be captured in this study if subjects present erythema scores of 2+ or higher and/or edema, and/or itching and/or papules even during a re-challenge.

Test Material

The test material used in this study was Comparison Formulation.

Study Protocol

The clinical protocols for this example follows the protocols set forth in Example 4A above.

Results

A total of 38 subjects completed the study. Table 10 below summarizes the number of subjects exhibiting each Dermal Score.

TABLE 10

Summary of Dermal Scores
Number of Subjects Exhibiting Each Dermal Score

| | Pre-Irradiation 24 Hour Patch Removal | | | | Post-Irradiation | | | | | | | | | | | |
|---|---|---|---|---|---|---|---|---|---|---|---|---|---|---|---|---|
| | | | | | Immediate | | | | 24 Hours | | | | 48 Hours | | | |
| Scores | I | NI | CI | CNI | I | NI | CI | CNI | I | NI | CI | CNI | I | NI | CI | CNI |
| 0 | 31 | 34 | 37 | 38 | 26 | 30 | 35 | 38 | 26 | 26 | 38 | 38 | 29 | 29 | 38 | 38 |
| ± | 7 | 4 | 1 | 0 | 8 | 5 | 3 | 0 | 10 | 10 | 0 | 0 | 7 | 7 | 0 | 0 |
| 1+ | 0 | 0 | 0 | 0 | 4 | 3 | 0 | 0 | 1* | 1* | 0 | 0 | 0 | 0 | 0 | 0 |
| 2+ | 0 | 0 | 0 | 0 | 0 | 0 | 0 | 0 | 1* | 1* | 0 | 0 | 2*, ** | 2*, ** | 0 | 0 |
| 3+ | 0 | 0 | 0 | 0 | 0 | 0 | 0 | 0 | 0 | 0 | 0 | 0 | 0 | 0 | 0 | 0 |
| 4+ | 0 | 0 | 0 | 0 | 0 | 0 | 0 | 0 | 0 | 0 | 0 | 0 | 0 | 0 | 0 | 0 |
| Total | 38 | 38 | 38 | 38 | 38 | 38 | 38 | 38 | 38 | 38 | 38 | 38 | 38 | 38 | 38 | 38 |

*1 site presented edema
** 1 site presented papule
I = Irradiated Site (Treated)
NI = Non-Irradiated Site (Treated)
CI = Control Irradiated Site
CNI = Control Non-Irradiated Site Confirmatory Patch Test A confirmatory patch test was performed on two subjects (Subjects 1 and 2). Subjects returned to the testing facility after 24 hours, 48 hours, 72 hours and 92 hours. Results for the confirmatory patch tests for 2 subjects are provided in Table 11 below.

TABLE 11

| Number of subjects | Test Material | 24 Hours | 48 Hours | 72 Hours | 96 Hours |
|---|---|---|---|---|---|
| 1 | Comparison Formulation | 2 + e | 2 + e | 2+ | 2+ |
| 2 | Comparison Formulation | 0 | ± | ± | 0 |

Conclusion

Under the conditions of this study, Comparison Formulation did not elicit a phototoxic response. However, two subjects exhibited erythema on both irradiated and non-irradiated sites. The erythema level on these subjects went from +/− at patch removal to 2+ at 48 hours along with papules and edema. These reactions are suggestive of pre-sensitization to the test material. The reactions erythema and edema observed during the confirmatory test, with the original product, confirmed that one subject was pre sensitized to the test material.

The invention claimed is:

1. A sprayable composition, wherein the composition comprises:
    (a) at least one active agent, wherein the at least one active agent comprises one or more sunscreen active agents;
    (b) a combination of film formers, wherein the combination of film formers comprises (i) one or more oil-soluble film formers and (ii) one or more alcohol-soluble film formers and/or one or more water-soluble film formers; and
    (c) at least one alcohol,
    wherein the composition is a sprayable sunscreen composition dispensable in the form of a spray, mist or fog.

2. The composition of claim 1, wherein the combination of film formers comprises one or more oil-soluble film formers and one or more alcohol-soluble film formers.

3. The composition of claim 1, wherein the one or more oil-soluble film formers comprise a polyester film former.

4. The composition of claim 1, wherein the one or more oil-soluble film formers comprise octyldodecyl/glyceryl hydroxy stearate dilinoleate dimethicone copolymer.

5. The composition of claim 1, wherein the one or more alcohol-soluble film formers comprise an acrylate film former.

6. The composition of claim 1, wherein the one or more alcohol-soluble film formers comprise a carboxylated acrylic copolymer.

7. The composition of claim 1, wherein the combination of film formers comprises octyldodecyl/glyceryl hydroxy stearate dilinoleate dimethicone copolymer and an alcohol-soluble carboxylated acrylic copolymer.

8. The composition of claim 1, wherein the combination of film formers comprises one or more oil-soluble film formers and one or more water-soluble film formers.

9. The composition of claim 1, wherein the combination of film formers comprises octyldodecyl/glyceryl hydroxy stearate dilinoleate dimethicone copolymer and acrylates/C12-22 alkylmethacrylate copolymer.

10. The composition of claim 1, wherein the one or more alcohols are present in a concentration of from 40% to 90% by weight of the composition, based on a total weight of the composition.

11. The composition of claim 1, wherein the one or more alcohols comprise ethanol.

12. The composition of claim 1, wherein the one or more oil-soluble film formers are present in a concentration of from 1% to 5% by weight of the composition and/or the one or more alcohol-soluble film formers are present in a concentration of from 1% to 5% by weight of the composition, based on a total weight of the composition.

13. A sprayable composition, wherein the composition comprises:
    (a) at least one active agent, wherein the at least one active agent comprises one or more sunscreen active agents;
    (b) two or more film formers, wherein the two or more film formers comprise (i) at least one oil-soluble film former, and (ii) at least one alcohol-soluble carboxylated acrylic copolymer; and
    (c) at least one alcohol,
    wherein the composition is a sprayable sunscreen composition dispensable in the form of a spray, mist or fog.

14. The composition of claim 13, wherein the at least one oil-soluble film former comprises a polyester having terminal silicone modifications.

15. The composition of claim 1, wherein the one or more sunscreen active agents comprise avobenzone, octocrylene, octisalate, and homosalate.

16. The composition of claim 1, wherein the composition further comprises at least one of a silicone fluid, a stabilizer, an emollient, and a solubilizer.

17. A method of making the composition of claim 1, wherein the method comprises:
    combining the one or more oil-soluble film formers with the one or more active agents to form a first mixture, wherein the first mixture comprises an oil phase;
    mixing and heating the first mixture until the oil phase of the first mixture is at least partially or fully dissolved; and
    adding at least one alcohol and at least one water-soluble film former to the first mixture to produce the composition.

18. A method of making the composition of claim 1, wherein the method comprises:
    combining the one or more oil-soluble film formers with the one or more active agents to form a first mixture, wherein the first mixture comprises an oil phase;
    mixing and applying heat to the first mixture until the oil phase of the first mixture is at least partially or fully dissolved;
    removing heat applied; adding at least one alcohol and at least one water-soluble film former to the first mixture to produce a second mixture; and
    mixing the second mixture until all ingredients therein are at least partially or fully dissolved to produce the composition.

* * * * *